United States Patent [19]

Wagner et al.

[11] 4,048,013

[45] Sept. 13, 1977

[54] PROCESS FOR PRODUCING SINGLE-CELL PROTEIN FROM METHANOL USING METHYLOMONAS SP. DSM 580

[75] Inventors: Fritz Wagner, Stockheim; Hermann Sahm, Wolfenbuttel, both of Germany

[73] Assignee: Gesellschaft fur Molekularbiologische Forschung mbH, Braunschweig, Germany

[21] Appl. No.: 694,792

[22] Filed: June 10, 1976

[51] Int. Cl.$^2$ ............................................... C12B 1/00
[52] U.S. Cl. ........................................ 195/49; 195/96
[58] Field of Search .................... 195/49, 96; 426/656

[56] References Cited

U.S. PATENT DOCUMENTS

| 3,878,045 | 4/1975 | Tannahill et al. .................... 195/49 |
| 3,989,594 | 11/1976 | MacLennan et al. ................. 195/49 |
| 3,994,781 | 11/1976 | Thorstensdotter .................... 195/49 |

FOREIGN PATENT DOCUMENTS

| 1,370,892 | 10/1974 | United Kingdom .................. 195/96 |
| 1,204,306 | 9/1970 | United Kingdom .................. 195/49 |

OTHER PUBLICATIONS

Thorstendotter, "Proteins from Methanol," Chemical Abstracts, vol. 79, No. 25, (1973), p. 206.

Haggstrom, "Protein for Human and Animal Consumption," Chemical Abstracts, vol. 81, No. 15, (1974), p. 357.

Ingestad et al., "Methanol-Containing Medium for Culture of Microorganisms," Chemical Abstracts, vol. 81, No. 7, (1974), p. 311.

*Primary Examiner*—Raymond N. Jones
*Assistant Examiner*—Thomas G. Wiseman
*Attorney, Agent, or Firm*—Haseltine, Lake & Waters

[57] ABSTRACT

A process for preparing a single cell protein from methanol is described. This process utilizes Methylomonas sp. DSM 580 as the obligate methanol-assimilating bacterium for the preparation of the single cell protein.

8 Claims, No Drawings

PROCESS FOR PRODUCING SINGLE-CELL PROTEIN FROM METHANOL USING METHYLOMONAS SP. DSM 580

The increasing demand for protein for human food and animal feed makes it necessary to develop new processes for producing lowcost protein with high nutritive value. During the past few years, much research was directed towards production of protein by microorganisms capable of utilizing gaseous hydrocarbons such as methane or liquid hydrocarbons resulting from petroleum fractions as a source of carbon and energy. Gaseous hydrocarbons, however, have the disadvantage of low solubility in an aqueous medium and explosion hazards associated with working under aerobic cultural conditions. Liquid hydrocarbons have the disadvantage of low water solubility too, which results in an increased energy consumption to disperse this substrate in the medium into small drops. Furthermore, it is necessary to refine the biomass which is produced on fluid hydrocarbons by solvent treatment in the final stage.

In the last few years, great interest has been shown in the development of processes for cultivation of microorganisms on a large scale with methanol as a particularly suitable source of carbon and energy. This substrate has the advantage that it can be easily and cheaply produced in a chemically defined form out of synthesis gas, which is obtainable from a very wide range of natural resources such as natural gas, petroleum and coal.

In DT-OS (German Offenugungschrift) 2,040,358, a process for producing single-cell protein is described using alcohols, aldehydes, ketones, carbonic acids and their derivatives as carbon sources formed by oxidation of liquid alkanes.

In DT-AS (German Auslegesschrift) 2,152,039, production of bacterial biomass in a culture medium containing methanol is described employing the following bacteria strains: Protaminobacter ruber var. machidanus ATCC 21 611, ATCC 21 612, ATCC 21 613 or ATCC 21 614.

In DT-OS 2,311,066, a process for producing single-cell proteins with the aerobic microorganism Methylomonas methanolica NRRL-B- 5458 cultivated in a medium containing methanol as the only carbon source is described.

In DT-OS 2,059,277, a microbial process for producing protein is described utilizing the following bacteria strains under aerobic conditions and methanol as the sole source of carbon: Pseudomonas methanica, Pseudomonas sp. ATCC 21 438, Pseudomonas sp. ATCC 21439, Pseudomonas sp. PRL-W 4, Corynebacterium sp. ATCC 21232, Corynebacterium sp. ATCC 21 235 and Corynebacterium sp. ATCC 21236.

In DT-OS 2,407,740, a process for cultivation of microorganisms is described, which comprises a mixed culture consisting of a facultative methanol-assimilating bacterium and several non-methanol assimilating bacteria. The methanol-assimilating bacterium is nonmobile and grows on methanol as well as on other organic compounds, for example, glucose and glycerine.

In DT-OS 2418385, a process for producing a product rich in protein is described employing a nonpink pigmented bacterial strain, which is a derivative of the microorganism Pseudomonas extorquens (NCIB Nr. 9399).

Until now, no obligate methanol assimilating bacterium has been employed for the production of protein from methanol, and only facultative methylotrophic microorganisms have been utilized. This stage of technology has been overcome by the invention using an obligate methylotrophic bacterium as a source of single-cell protein.

From a soil sample collected at the Rheinufer Ludwigshafen, an obligate methanol-assimilating bacterium was isolated by enrichment culture. 1 g of the soil sample was suspended in 100 ml of a mineral salt medium of the following composition: $KH_2PO_4$, 3.75 g; $Na_2HPO_4$, 2.5 g; $(NH_4)_2SO_4$, 4.0 g; $MgSO_4.7H_2O$, 0.5 g; $Ca(NO_3)_2.4H_2O$, 0.025 g; $FeSO_4.7H_2O$, 0.005 g; $ZnSO_4.H_2O$, 0.005 g, in 1000 ml distilled water, pH 7, with 1% (v/v) methanol and incubated in 500 ml flasks on a rotary shaker at 100 rpm at 30° C. The inoculated medium was cultured for five days and then 0.1 ml of it was streaked on nutrient agar plates with the same medium except with 2% agar. After repeated selections of single colonies from agar plates and cultivation in liquid cultures a pure bacterium, designated Methylomonas sp., with the Nr. DSM 580, was obtained. It is an object of the present invention to provide a process for a methanol-based production of single-cell protein. The process for production of single-cell protein according to the invention comprises inoculating a sterile liquid medium with a culture of the obligate methanol-assimilating bacterium Methylomonas sp. DSM 580 containing assimilable sources of nitrogen, methanol as the sole source of carbon and energy, essential mineral salts and, if necessary, growth-promoting agents. The fermentation is carried out under aerobic conditions providing the system with air or oxygen enriched air, the cultivating temperature is from 20°-45° C. After culturing, the microbial cells are removed out of the three phase system and dried, presenting a biomass with a crude protein content from 60-70% (w/w), a nucleic acid content from 2-17% (w/w), an ash content of 3-6% (w/w) and a lipid content from 3-8% (w/w). The culture fluid removed in the separation step may be recycled back in the process.

The microorganism suitable for use in the present invention is the methanol-assimilating bacterium Methylomonas sp. DSM 580 with the following morphological and cultural characteristics:

1. Cell morphology: Non spore forming short rod measuring approximately 0.5 × 1.5 μm, highly motile with a single polar flagellum. In liquid culture the cells are slightly pink, (while after centrifugation the cell pellet is intensively pink).
2. Colony characteristics: Translucent, nonpigmented, circular, smooth, 1 - 2 mm diameter after 2-3 days incubation.
3. Staining reaction: gram - negative
4. Physiology: aerobic, catalase positive, methanol dehydrogenase positive, hexose - phosphate-synthetase positive, hydroxypyruvate - reductase negative.
5. Growth characteristics:

|  | min. | optimum | maximum |
|---|---|---|---|
| Temperature (° C) | 20 | 33–36 | 45 |
| pH | 4.5 | 6.5–7.5 | 9.5 |
| Methanol conc. % (v/v) |  | 0.5–1.5 | 5.0 |

The described bacterium Methylomonas sp. is deposited at the German collection of microorganisms, Göttingen, with the number DSM 580.

Methylomonas sp. DSM 580 is an obligate methylotrophic bacterium i.e., only methanol supports its growth. Growth was not observed when $C_1$-compounds other than methanol or when some other substrates were tested (Table I). Table I: Growth of Methylomonas sp. DSM 580 on various carbon sources in mineral salt medium under aerobic conditions.

| Substrate | Growth[1] |
| --- | --- |
| Methane | − |
| Methanol | + |
| Methylamine | − |
| Formaldehyde | − |
| Sodium Formate | − |
| Ethanol | − |
| Propanol-(1) | − |
| Propanol-(2) | − |
| Sodium Acetate | − |
| Sodium Lactate | − |
| Sodium Pyruvate | − |
| Sodium Succinate | − |
| Sodium Citrate | − |
| Glucose | − |
| Fructose | − |
| Serine | − |

[1]+ growth − no growth

Furthermore, it was determined that Methylomonas sp. DSM 580 is cultivated in a batch culture with an initial methanol concentration from 0.5 − 5% (v/v), preferably from 2–3% (v/v) and that Methylomonas sp. DSM 580 is cultivated in a batch culture where the methanol concentration is maintained from 0.01–2.0% (v/v), by an automatic control system and 25% (v/v) methanol is consumed.

It was also determined that Methylomonas sp. DSM 580 is cultivated in a continuous culture at a dilution rate from 0.1–0.5 vol/vol/h under chemostatic or turbidostatic conditions.

Furthermore, it was determined that, throughout the fermentation, a constant pH was adjusted in the range of from 4.5–9.0 by adding alkali or acids.

It was also determined that Methylomonas sp. DSM 580 is cultivated at a temperature from 20°–45° C, preferably from 33°–36° C.

Furthermore, it was determined that throughout the fermentation the fermenter is supplied with air or oxygen enriched air with an aeration rate from 0.5–1.5 vol/vol/min and that the gas mixture has an oxygen content of 20–60% v/v).

It was also determined that the aqueous culture medium contains ammonium and/or nitrate salts of inorganic acids and/or urea as assimilable sources of nitrogen and the essential cations such as sodium, potassium, magnesium, calcium, iron, zinc, manganese and the anions such as phosphate, sulfate, nitrate, chloride and growth promoting agents.

As used herein, nutrient substances are chemical compounds, which contain, besides the carbon and energy source, anions and cations which are taken up by the microorganisms and are necessary for their growth. Growth promoting agents are natural or synthetic compounds, which are required by the microorganisms but could not be synthetized by these organisms in sufficient amounts.

The invention is now illustrated in the following examples:

EXAMPLE 1

A 80 l capacity fermenter is charged with 50 l mineral salt medium (composition: $(NH_4)_2SO_4$, 200 g; $KH_2PO_4$, 150 g; $Na_2HPO_4$ 125 g; $MgSO_4.7H_2O$, 25 g; $Ca(NO_3)_2.4H_2O$, 1.25 g; $FeSO_4.7H_2O$, 0.25 g; $ZnSO_4.H_2O$, 0.25 g; KCl, 0.25 g in 50 l distilled water) and sterilized at 121° C for 10 minutes, cooled to 15° C, aseptically mixed with 1000 ml methanol, inoculated with 500 ml of a culture of Methylomonas sp. DSM 580 and incubated at 35° C for 28 hours under stirring with a turbostirrer with a stirring rate of 300 rpm and a aeration rate of 0.7 vol/vol/min. Throughout the fermentation the pH is automatically maintained at 6.4 by the addition of a 6% ammonium hydroxide solution. After 22 hours of fermentation, the medium is cooled to 15° C and adjusted to pH 3 by sulfuric acid and the precipitated biomass is recovered by filtration, washed with water and then dried (324 g cell dry weight). The cell composition of the dried biomass is: 71% crude protein, 9% nucleic acids, 4% ash and 7% lipid.

EXAMPLE 2

A 340 l fermenter, fitted with an "intensor," produced by Biologische Verfahrenstechnik AG, Basle, is charged with 200 l mineral salt medium (compounds: 500 g $(NH_4)_2SO_4$, 500 g $NH_4NO_3$, 600 g $KH_2PO_4$, 500 g $Na_2HPO_4$, 140 g $MgSO_4.7H_2O$, 15 g $Ca(NO_3)_2.4H_2O$, 6 g $FeSO_4.7H_2O$, 2 g KCl in 200 l tap water), the pH is adjusted to 6.8, sterilized for 15 minutes at 121° C, cooled down to 33° C, 2000 ml methanol were added aseptically, inoculated with 4000 ml culture of Methylomonas sp. DSM 580 grown for 18 hours in the same medium, and incubated at 33° C with the aeration rate of 0.5% (v/v) in the culture medium, methanol concentration was kept constant at 0.5% (v/v) by measuring continuously the vaporconcentration of methanol, which is in relation with the concentration of methanol in the medium; furthermore the pH is maintained at 6.8 by automatic addition of 12% (v/v) ammoniumsolution. After an incubation of 25 hours the cell concentration is 14 g dry weight/l, now the fermenter is aerated with oxygen enriched air with an oxygen content of 40% (v/v), while the aeration rate is the same as above. After 60 hours, the fermenter is cooled down to 15° C, the cells were harvested by a high-speed continuous flow centrifuge at 10,000 g and dried. Under these process-conditions, the cell yield is 0.44 g dry weight/g methanol and these dried cells contain 76% crude protein, 6.5% nucleic acids, 5% ash and 4.5% lipid.

EXAMPLE 3

A 80 l fermenter with an intensor as described in Example 2 is charged with 50 l culture medium the same as in Example 1, inoculated with 1000 ml culture of Methylomonas sp. DSM 580, which was grown 15 hours at 35° C, cultivated at 35° C, an aeration rate of 0.5 vol/vol/min, the stirrer speed of 1200 rev/min and a constant pH at 7.0. The continuous culture is started after 18 hours with a dilution rate of 0.05, which is increased after 48 hours to 0.1, and then within 120 hours by steps to 0.35. Under these conditions, a steady state is possible, the cell yield is 0.46 g dry weight/g methanol and the production is 10.8 g/l/h. The cell composition is 72% crude protein, 4.5% nucleic acids, 3.5% ash and 5.5% lipid. Under steady state conditions, 50% of the culture filtrate is recycled back and the added culture medium is reduced to this amount.

The present invention generally possesses the advantage that for the first time an obligate methylotrophic baterium is used as process organism with a significant higher productivity than other known facultative methylotrophic microorganisms have. Furthermore, no undesirable mutation of this microorganism involved in the present process can occur which may affect the ability of growing on methanol. This bacterium is very stable, its metabolism is reduced to a minimum and genetic variations would cause death of the cells. Another advantage of the present invention is that the key enzymes of the dissimilation and assimilation pathways of methanol are constitutive in Methylomonas sp. DSM 580. In the case of methanol-limited conditions in continuous culture, the nucleic acid content in the cells is very low and there is practically no loss of methanol through evaporation.

We claim:

1. A process for the production of single-cell protein from methanol, which comprises placing, in an aerated fermenter with or without a mechanical stirrer, a growing submerged culture of the obligate methanol-utilizing bacterium Methylomonas sp. DSM 580, produced under aerobic conditions, cultivating it in the presence of methanol, used as the sole source of carbon and energy, and mineral salts, in the presence or absence of growth promoting agents, this system further provided with air or oxygen enriched air at a cultivating temperature from 20° to 45° C, thereafter removing the cell mass out of the three phase system and drying, resulting in a biomass with a crude protein content of at least 60–76% (w/w), a nucleic acid content of 2–17% (w/w), an ash content of 4–6% (w/w), a lipid content of 3–8 (w/w), the culture fluid, after removing the cell mass, is capable of being, at least partially, recycled.

2. A process according to claim 1 for the production of single cell protein from methanol which comprises placing, in an aerated fermenter with or without a mechanical stirrer, a growing submerged culture of the obligate methanol-utilizing bacterium Methylomonas sp. DSM 580, produced under aerobic conditions, cultivating it in the presence of methanol used as the sole source of carbon and energy, the aqueous culture medium containing compounds selected from ammonium salts, nitrate salts, urea and mixtures thereof as nitrogen source, salts selected from those containing cations, selected from sodium, potassium, magnesium, calcium, iron, and manganese, anions selected from phosphate, sulfate, nitrate and chloride in the presence or absence of growth promoting agents, this system being provided with air or oxygen enriched air, at a cultivating temperature from 20° to 45° C, thereafter removing the cell mass of the three phase system and drying, resulting in a biomass with a crude protein content of at least 60–76% (w/w), a nucleic acid content of 2–17% (w/w), an ash content of 3–6% (w/w), a lipid content of 3–8% (w/w) the culture fluid, after removing the cell mass is capable of being, at least partially, recycled.

3. A process according to claim 2 in which Methylomonas sp. DSM 580 is cultivated in a batch-culture with an initial methanol concentration from 0.5–5% (v/v), preferably from 2–3% (v/v).

4. A process according to claim 2 in which Methylomonas sp. DSM 580 was cultivated in a batch-culture, where the methanol concentration is maintained at from 0.01–2% (v/v) by an automatic control system and 25% methanol (v/v) is consumed.

5. A process according to claim 2 in which Methylomonas sp. DSM 580 is produced continuously in a chemostatic or turbidostatic culture at a dilution rate of from 0.1–0.5 v/v/h.

6. A process according to claim 2 in which the pH is adjusted automatically in the range from 4.5–9.0 by adding alkali or acids throughout the fermentation.

7. A process according to claim 2 in which the fermenter is supplied with air or oxygen enriched air throughout the fermentation with an aeration rate from 0.5–1.5 v/v/min and the gas mixture has an oxygen content of 20–60% (v/v).

8. A process according to claim 2 in which the fermentation vessel is supplied with air or oxygen enriched air, with an aeration rate from 0.1–0.2 v/v/min and the gas mixture has an oxygen content of 20–60% (v/v).

* * * * *